(12) United States Patent
Liu

(10) Patent No.: US 7,321,117 B2
(45) Date of Patent: Jan. 22, 2008

(54) OPTICAL PARTICULATE SENSOR IN OIL QUALITY DETECTION

(75) Inventor: James Z T Liu, Hudson, NH (US)

(73) Assignee: Honeywell International Inc., Morristown, NJ (US)

( * ) Notice: Subject to any disclaimer, the term of this patent is extended or adjusted under 35 U.S.C. 154(b) by 218 days.

(21) Appl. No.: 11/234,606

(22) Filed: Sep. 22, 2005

(65) Prior Publication Data

US 2007/0063140 A1    Mar. 22, 2007

(51) Int. Cl.
*G01T 1/169*    (2006.01)

(52) U.S. Cl. .................................... 250/301
(58) Field of Classification Search ............ 250/301
See application file for complete search history.

(56) References Cited

U.S. PATENT DOCUMENTS

| | | | |
|---|---|---|---|
| 5,489,977 A | 2/1996 | Winslow et al. | |
| 5,574,738 A | 11/1996 | Morgan | 372/28 |
| 5,764,674 A | 6/1998 | Hibbs-Brenner et al. | 372/46 |
| 5,774,487 A | 6/1998 | Morgan | 372/45 |
| 5,893,722 A | 4/1999 | Hibbs-Brenner et al. | 438/45 |
| 5,978,401 A | 11/1999 | Morgan | 372/50 |
| 6,069,905 A | 5/2000 | Davis et al. | 372/43 |
| 6,411,638 B1 | 6/2002 | Johnson et al. | 372/46 |
| 6,519,034 B1 | 2/2003 | Engler et al. | 356/338 |
| 6,674,777 B1 | 1/2004 | Nohava et al. | 372/44 |
| 6,678,300 B2 | 1/2004 | Johnson et al. | 372/46 |
| 6,693,934 B2 | 2/2004 | Wang | 372/43 |
| 6,700,130 B2 * | 3/2004 | Fritz | 250/573 |
| 6,712,273 B1 | 3/2004 | Stapleton et al. | 235/462.49 |
| 6,717,667 B2 | 4/2004 | Abraham et al. | 356/318 |
| 6,718,819 B2 | 4/2004 | Schoess | 73/53.05 |
| 6,787,756 B2 | 9/2004 | Tatum et al. | 250/221 |
| 6,817,528 B2 | 11/2004 | Chen | |

(Continued)

FOREIGN PATENT DOCUMENTS

JP    2003038163 A   *   2/2003

(Continued)

OTHER PUBLICATIONS

Veuhoff E., Potential of MOMBE/CBE for the Production of Photonic Devices in Comparison with MOVPE, Journal of Crystal Growth, Amsterdam, NL, vol. 188, No. 1-4, 1998, p. 231-246.
Liu, James, *Smoke Alarm Photo-Chamber Design Theory and Analysis*, Honeywell, Aug. 25, 2003.

*Primary Examiner*—David Porta
*Assistant Examiner*—Marcus H Taningco
(74) *Attorney, Agent, or Firm*—Kermit D. Lopez; Luis M. Ortiz; William B. Shelby

(57) ABSTRACT

An oil quality sensor apparatus includes a housing that includes an oil flow path through which oil flows through the housing. One or more photo-detectors can be provided in association and a plurality of light-emitting devices located within the housing and proximate to the oil flow path. At least one light-emitting device among the plurality of light-emitting devices is sensitive to large particulates associated with the oil and at least one other light-emitting device among the plurality of light-emitting devices is sensitive to small particulates associated with the oil to thereby provide an indication of differences among particulates associated with the oil.

20 Claims, 3 Drawing Sheets

U.S. PATENT DOCUMENTS

| | | |
|---|---|---|
| 6,875,993 B2 | 4/2005 | Tatum et al. ............ 250/559.2 |
| 2003/0060984 A1 | 3/2003 | Takezawa et al. |
| 2003/0138020 A1 | 7/2003 | Chen ........................... 372/75 |
| 2004/0101009 A1 | 5/2004 | Johnson et al. ............... 372/45 |
| 2004/0264530 A1 | 12/2004 | Ryou et al. ................... 372/44 |
| 2004/0264541 A1 | 12/2004 | Wang et al. ................... 372/99 |

FOREIGN PATENT DOCUMENTS

| | | |
|---|---|---|
| WO | WO 91/18280 A1 | 11/1991 |
| WO | WO 00/09985 A2 | 2/2000 |

* cited by examiner

OPTICAL PARTICULATE SENSOR IN OIL QUALITY DETECTION

TECHNICAL FIELD

Embodiments are generally related to sensor methods and systems. Embodiments are also related to optical detection devices. Embodiments are additionally related to back-scattered particulate sensors. Embodiments also relate to methods and systems for liquid turbidity sensing applications. Embodiments additionally relate to oil quality sensing methods and systems.

BACKGROUND

Detecting oil contamination and deterioration, in an internal combustion engine, is important in promoting and prolonging the useful life of the engine and engine oil.

The usable life of motor oil depends on many factors, including the type of oil used, the engine's condition, ambient operating conditions, driving habits, vehicle usage, and vehicle servicing. While most car manufacturers recommend changing the engine oil of an automobile at three months or three thousand miles, whichever comes first, many automobile owners and operators fail to regularly change the engine oil of their automobile within the recommended time frame.

Where deteriorated oil is subject to prolonged use because of infrequent oil changes, the useful life of an automobile engine is greatly reduced. The useful life of an automobile engine may also be reduced by the introduction of contaminants in the engine oil such as: water, antifreeze, or improper types of oil (e.g. four-stroke oil in a two-stroke engine). Accordingly, some types of oil monitoring methods and equipment, for detecting deterioration and contamination of engine lubricating oil, have been created.

Engine oil may contain fine carbon particulates (e.g., 0.03 µm to 0.05 µm) and larger metal particulates (e.g., 3 µm to 5 µm). It is therefore very important to determine the type and the quantity of such particulates. Prior art sensors are adequate for some oil quality detection application. Generally, however, such sensors have difficulty in detecting particulates, particularly because the sensing results are lumped into an overall detection data category and it is difficult to determine types of particulates and the varying particulate sizes. It is believed that a solution to this problem involves implementing the improved detection devices and techniques disclosed in greater detail herein. Optical scattering sensors, i.e., smoke alarms and turbidity sensors could be used as particulate sensors but they are sensing the lumped result and can't tell the difference among particulates with different sizes.

BRIEF SUMMARY

The following summary is provided to facilitate an understanding of some of the innovative features unique to the embodiments and is not intended to be a full description. A full appreciation of the various aspects of the embodiments disclosed can be gained by taking the entire specification, claims, drawings, and abstract as a whole.

It is, therefore, one aspect of the present invention to provide for improved sensor methods and systems.

It is another aspect of the present invention to provide for an improved oil quality sensor.

It is a further aspect of the present invention to provide for an oil quality sensor apparatus that incorporates the use of light-emitting devices, such as, for example, a Vertical Cavity Surface Emitting Laser (VCSEL) and/or a light emitting diode (LED).

The aforementioned aspects of the invention and other objectives and advantages can now be achieved as described herein. An oil quality sensor apparatus is disclosed, which generally includes a housing configured to include a hole through which oil enters the housing and an oil flow path that the oil flows through the housing. One or more photodetectors can be provided in association and a plurality of light-emitting devices located within the housing and proximate to the oil flow path. At least one light-emitting device among the plurality of light-emitting devices is sensitive to large particulates associated with the oil and at least one other light-emitting device among the plurality of light-emitting devices is sensitive to small particulates associated with the oil to thereby provide an indication of differences among particulates associated with the oil.

The light-emitting devices can be provided as, for example, a VCSEL, LED and/or EEL. When the wavelength of a VCSEL (e.g., LED, for example) is close to the average size of the particulates in the oil, Mie-Debye scattering is stronger than Rayleigh scattering and light-scattering sensors thereof have a high sensitivity to particulates with diameters approximately equal to the VCSEL wavelength, and low sensitivity to particulates much smaller than the VCSEL wavelength. In one embodiment, since carbon and metal particulates have larger size difference, two VCSELs (or LED) can be utilized. One VCSEL can provided as an IR VCSEL, and the other VCSEL can be implemented as a UV VCSEL (e.g., 130 nm, 100 nm or even smaller). In general, The IR VCSEL is sensitive to larger particulates such as, but not limited to, for example, metal; while the UV VCSEL is sensitive to smaller particulates, such as, but not limited to carbon particulate.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the principles of the disclosed embodiments.

DETAILED DESCRIPTION

The particular values and configurations discussed in these non-limiting examples can be varied and are cited merely to illustrate at least one embodiment and are not intended to limit the scope of the invention.

The disclosed embodiments can be implemented in the context of an oil quality sensor apparatus, which generally includes a housing configured to include a hole through which oil enters the housing and an oil flow path that the oil flows through the housing. One or more photo-detectors can be provided in association and a plurality of light-emitting devices located within the housing and proximate to the oil flow path. At least one light-emitting device among the plurality of light-emitting devices is sensitive to large particulates associated with the oil and at least one other light-emitting device among the plurality of light-emitting devices is sensitive to small particulates associated with the oil to thereby provide an indication of differences among particulates associated with the oil.

One example of a light-emitting device that can be implemented in accordance with a preferred embodiment is a Vertical Cavity Surface Emitting Laser (VCSEL). In general, a VCSEL can offer high-quality +/−2° beam. VCSEL die placement is repeatable, creating a device with a max beam tolerance of approximately +/−5°. This allows the photo-detector(s) to be placed very close to the incident beam, or the photo-detector(s) to be placed at a much smaller scatter angle, thereby increasing the intensity of scattered light. By reducing the distance between scatter particles to a photo-diode by half, for example, an increase in the intensity thereof can be obtained at a parameter of, for example, 4 times. In Rayleigh scattering theory or approximation, particles are optically similar to the surrounding medium. Rayleigh scattering is strong forward-backward asymmetry. Except for very small particles, scattering is peaked in the forward direction. The larger the particle, the sharper the peak.

There is no single answer for why light is scattered. Scattering by particles has been treated by classical electromagnetic theory. A particle is an aggregation of many molecules. While light is an oscillating electromagnetic field, which can excite the charges in matter to oscillate. A single particle can be considered a collection of tiny dipole antennas driven to radiate (scatter) by an incident oscillating electric field. Scattering by such a coherent array of antennas depends on its size and shape, the scattering angle, the composition, the polarization state, and the frequency of the incident light wave. The geometry, composition of the particle and the properties of the light (frequency, intensity, etc.) determine scattering by particle.

Figure 1:
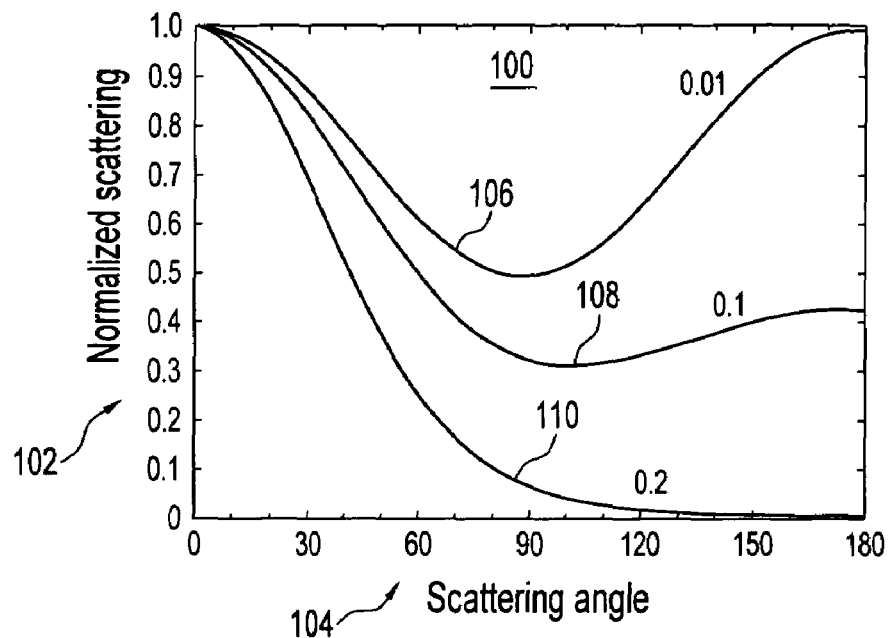
FIG. 1 illustrates a graph depicting differential scatting cross sections and various scattering angles for light emitting spheres of various radii, in accordance with a preferred embodiment.

In Rayleigh scattering theory (or an approximation thereof), particles are optically similar to the surrounding medium. Rayleigh scattering is strong forward-backward asymmetry. Except for very small particles, scattering is peaked in the forward direction. The larger the particle, the sharper the peak. FIG. 1 shows differential scattering cross sections for unpolarized light illuminating spheres of various radii. Forward scattering is much greater than backscattering even for a sphere as little as 0.2 μM. Particles are very small polarizers and retarders.

FIG. 1, for example, illustrates a graph 100 depicting differential scatting cross sections and various scattering angles for light emitting spheres of various radii, in accordance with a preferred embodiment. Graph 100 depicted in FIG. 1 generally includes a y-ordinate 102 associated with normalized scattering data and an x-ordinate 104 associated with scattering angle data. Lines 106, 108, 110 plotted in graph 100 indicate varying results in a respective range of 0.01, 0.1 and 0.2.

In general, when a shorter distance and a smaller angle can be obtained for a stronger scattered signal by using a VCSEL, the noise from ambient light source is not changed. This would enable the elimination of the photo-chamber cover, baffles, air-inlets, vanes, etc.. Size and cost play important roles, especially since housing materials makes up a sizable portion of a sensor's cost. Unlike conventional edge-emitting laser diodes, a VCSEL's optical beam is perpendicular to the chip surface. This not only simplifies device fabrication and testing—which lowers production costs—it also creates smaller structures that consume less power.

In Mie scattering theory, for example, the scatter particles are considered as isotropic, finite and homogeneous. Mie scattering is not a physical process. It is not exact because it is based on continuum electromagnetic theory. There is no sharp boundary between Rayleigh and Mie theories. Mie theory includes Rayleigh theory, which is a limiting theory strictly applicable only as particle size shrinks to zero. Whether a particle is a Mie or Rayleigh scatterer is not absolute. A particle may be changed from a Rayleigh to a Mie status merely by a change of wavelength of the light (i.e., when wavelength, $\lambda$, change to shorter.)

VCSEL reliability and MTTF (Mean time to failure) data have demonstrated that a VCSEL has orders higher MTTF than that of LEDs. VCSEL has better reliability than LED. For nominal operating conditions of 40C and 2 mW power, the VCSEL is about 100 to 1000 times more reliable than an EEL. In a VCSEL, laser photons bounce between mirrors grown into the structure and then emit vertically from the wafer surface. VCSELs, which can be grown by the thousands on a single wafer, have significant advantages over edge-emitting lasers in the areas of lower manufacturing, packaging, alignment, and testing costs, as well as lower power dissipation and higher reliability.

Figure 2:
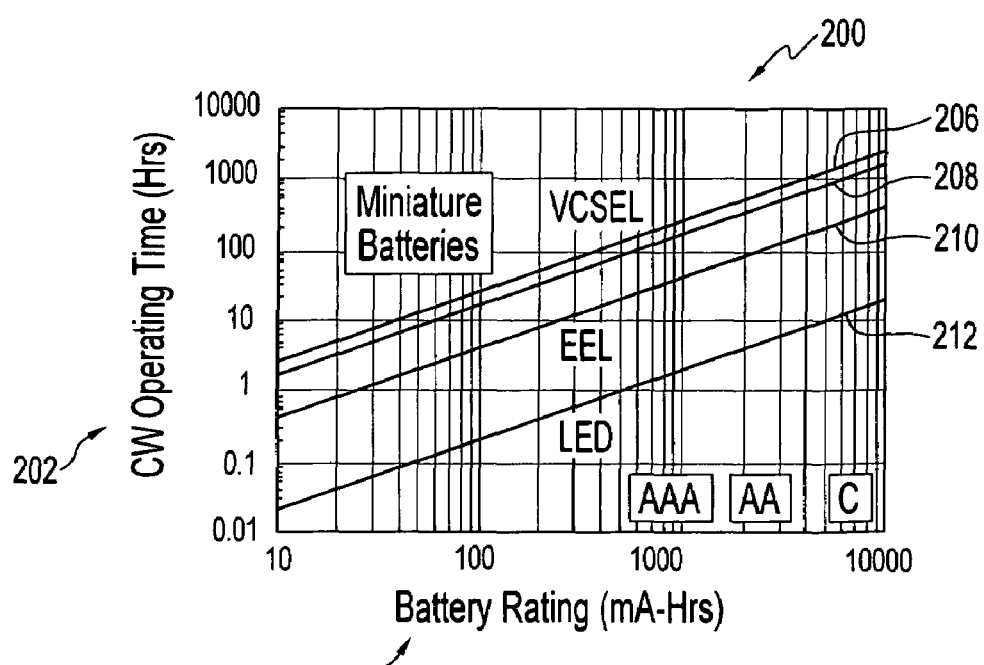
FIG. 2 illustrates a graph depicting a plot of operations associated with varying optical sources as a function of battery rating, in accordance with a preferred embodiment.

VCSELs operate in a single spatial and longitudinal mode. The primary advantages from using a single mode VCSEL, for example, include an enhanced battery lifetime, high optical beam quality, and extremely high degree of coherence. Battery lifetime is a significant issue when one considers the use of optical components in consumer electronics applications. FIG. 2, for example, illustrates a graph 200 depicting a plot of operations associated with varying optical sources as a function of battery rating, in accordance with a preferred embodiment. Graph 200 generally includes a y-ordinate 202, which is indicative of operating time (hours), while an x-ordinate 204 provides data indicative of battery rating data (mA-Hrs).

Data associated with miniature batteries is thus depicted in graph 200 with respect to lines 206, 208, which are associated with a VCSEL; line 210, which is associated with an edge-emitting laser (EEL); and line 212, which is associated with a light-emitting diode (212). As can be seen from graph 200, the battery life associated with a VCSEL is preferred. Graph 200 thus functions as a plot of operating lifetime (defined as emitting 1 mW of optical power into a cone angle of 30 degrees) of various optical sources as a function of battery rating. Thus, several commonly used battery types (i.e., VCSEL, EEL, and LED) are indicated on the graph as well. Using a VCSEL source can increase battery lifetime by nearly an order of magnitude, which is a significant concern to the end user.

Figure 3:
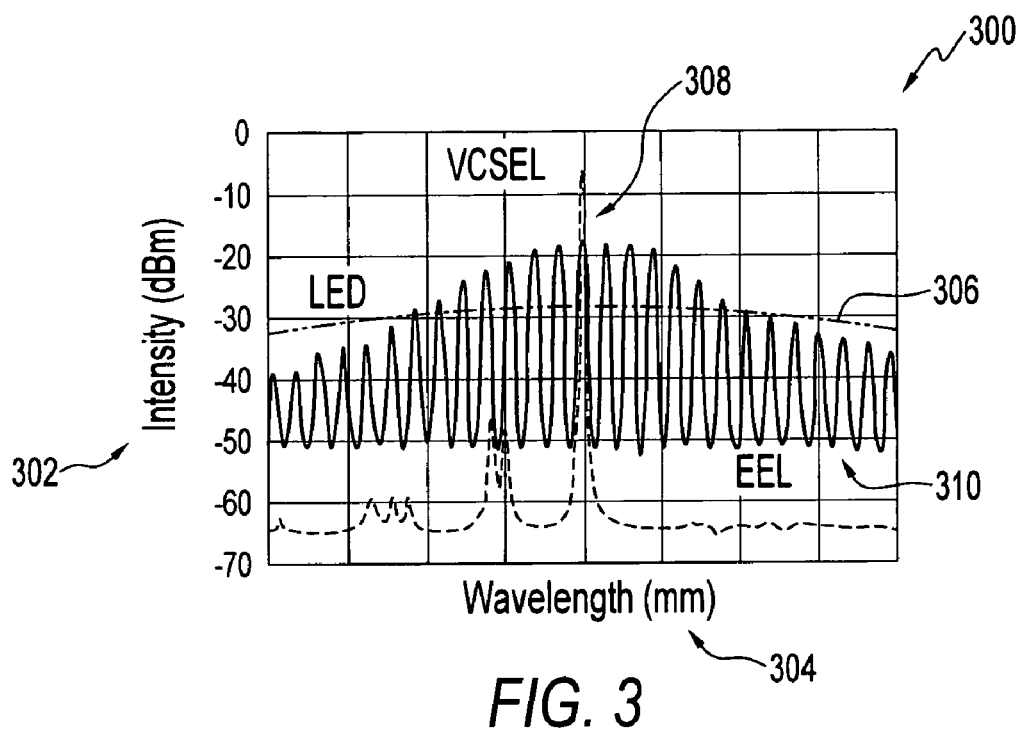
FIG. 3 illustrates a graph depicting the optical spectrum of an LED, an EEL and a VCSEL, which can be implemented in accordance with varying embodiments.

FIG. 3 illustrates a graph 300 depicting the optical spectrum of an LED, an EEL and a VCSEL, which can be implemented in accordance with varying embodiments. Graph 300 includes a y-ordinate 302 indicative of intensity data and an x-ordinate indicative of wavelength in nanometers. Plots 308, 306 and 310 provide data respectively associated with a VCSEL, an LED and an EEL. For applications where coherence and/or a specific wavelength of laser emission are important, VCSELs offer significant advantages over other light sources such as LEDs and EELs. Graph 300 thus represents a plot of the optical spectrum of a VCSEL, an LED and an EEL showing the differences in spectral purity of the optical source. This is particularly important when one is looking at sensing coherent effects such as laser speckle, or using the laser source as a wavelength sensitive optical sensor.

Table 1 below summarizes some of the traits of various light sources that may be important in developing sensing applications.

TABLE 1

Summary of relevant optical characteristics for several sources for sensing applications.

| Attribute | Symbol | Units | SM VCSEL | MM VCSEL | EE Laser | LED |
|---|---|---|---|---|---|---|
| Electrical Power | $P_{elec}$ | mW | 5 | 20 | 60 | 60 |
| Optical Power | $P_{opt}$ | mW | 1 | 5 | 10 | 1 |
| Efficiency at Popt = 1 mW | $\eta$ | % | 20 | 10 | 5 | 2* |
| Wavelength | $\lambda$ | nm | 760-860 | 670-870 | 630-1300 | 400-1300 |
| Spectral Width | $\Delta\lambda$ | nm | 0.01 | 0.5 | 2 | 50 |
| Spectral Tuning (Temperature) | $\Delta\lambda/\Delta T$ | nm/° C. | 0.06 | 0.06 | 0.3 | 0.3 |
| Spectral Tuning (Current) | $\Delta\lambda/\Delta I$ | nm/mA | 0.25 | 0.09 | | |
| Beam Angle (full width at half of maximum value) | ∠ | ° | <15 | ~15 | 15 par. 35 perp | 120 |

Figure 4:
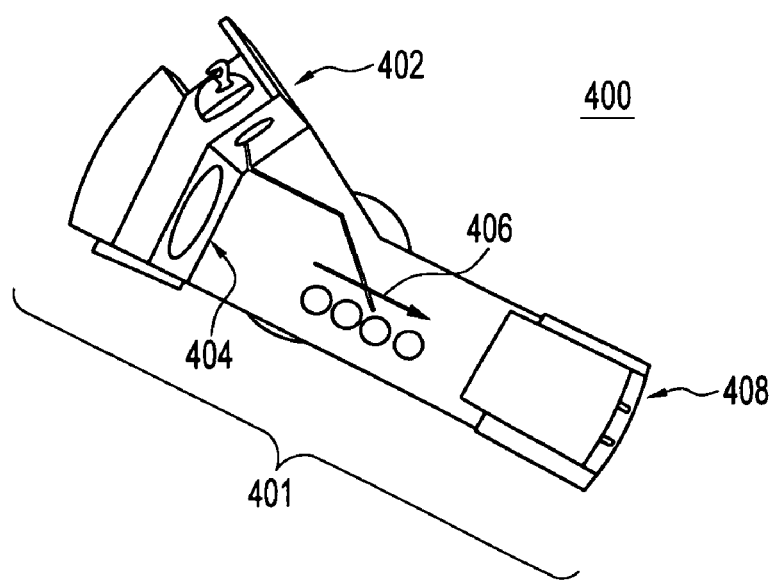
FIG. 4 illustrates a diagram of an oil particulate sensor apparatus, which can be implemented in accordance with a preferred embodiment.

FIG. 4 illustrates a diagram of a oil particulate sensor apparatus 400, which can be implemented in accordance with a preferred embodiment. The oil quality sensor apparatus 400 includes a housing 401 that is configured to include a hole 404 through which oil enters the housing 401 and an oil flow path 406 that the oil flows through the housing 401. One or more photo-detectors 402 can be provided in association and one or more light-emitting devices 408 located within the housing 401 and proximate to the oil flow path 406. Note that photo-detector(s) 402 can be configured as a plurality of photo-diodes wherein each photo-diode among the photo-diodes possesses a different wave-length.

The light-emitting device 408 can be implemented in the context of one or more light emitting devices 408 (e.g., VCSEL, LED etc), such that as least one light-emitting device among the plurality of light-emitting devices 408 is sensitive to large particulates associated with the oil and at least one other light-emitting device among the plurality of light-emitting devices 408 is sensitive to small particulates associated with the oil to thereby provide an indication of differences among particulates associated with the oil. Light-emitting device 408 can be implemented as, for example, one or more LED's and/or one or more VCSELs. If a VCSEL, for example, the VCSEL(s) 408 and the photo-detector 402 are preferably located in association with housing 401, such that the light from the VCSEL(s) 408 will not be detected when there is no scattered light from certain particles associated with oil flowing along oil flow path 406.

Figure 5:
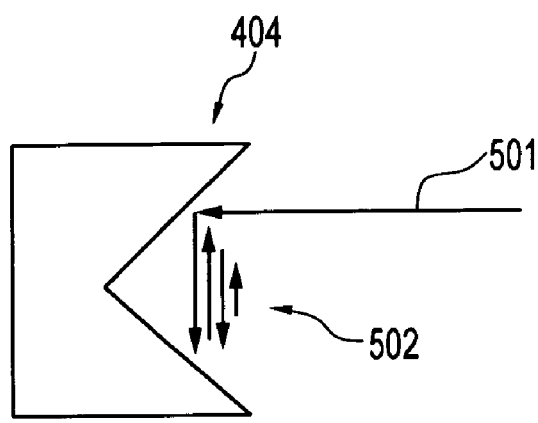
FIG. 5 illustrates a diagram of the "black hole" depicted in FIG. 4, in accordance with a preferred embodiment.

FIG. 5 illustrates a diagram of the "black hole" 404 depicted in FIG. 4, in accordance with a preferred embodiment. In general, the hole 404 can be referred to as constituting a "black hole". In one configuration, the black-hole 404 can be configured as an inverted-cone, the angle of the cone selected such that the reflected light would be reflected as many times as possible within the cone before such light is bounced out. A preferred angle is, for example, 45 degrees. In other configurations and alternative embodiments, the black-hole 404 can be configured as a cylindrical or other shape, but the wall facing the VCSEL(s) 408 can be 45 degrees instead of 90 degrees. FIG. 5 thus illustrates a possible cross-section of black-hole 404 and how incident light can be bounced within the black-hole 404, as indicated by arrows 501 and 502.

Figure 6:
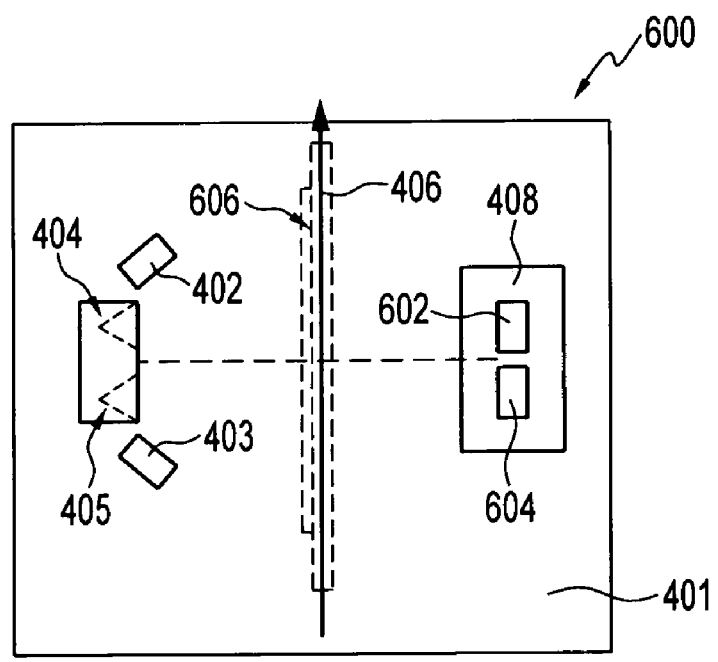
FIG. 6 illustrates a diagram of a sensor apparatus, which can be implemented in accordance with an alternative embodiment.

FIG. 6 illustrates a diagram of a sensor apparatus 600, which can be implemented in accordance with an alternative embodiment. Note that in FIGS. 5-6, like or identical parts or elements are generally indicated by identical reference numerals. Sensor apparatus 600 thus generally includes the light-emitting device 408 indicated in FIG. 4. In the configuration of FIG. 6, however, light-emitting device 408 is provided as a plurality of VCSELs, i.e., an IR VCSEL 602 and a UV VCSEL 604. Note that each VCSEL among the plurality of VCSELs can be configured to operate with different wave-lengths. The same holds true when other light-emitting devices such as LEDs or edge-emitting lasers are utilized in place or in association with VCSELs.

Oil 606 is also shown in FIG. 6 as flowing along oil flow path 406. The other parts (e.g., black holes 404, 405, photo detectors 402, 403, and housing 401) indicated in FIG. 4 are also illustrated in FIG. 6. Note that housing 401 may be implemented in the context of a number of potential housing configurations, such as, for example, a substrate or a Printed Circuit Board (PCB), or a plastic trace, depending upon design considerations. Oil 606 may be composed of a number of particulates, include particulates such as metal and/or carbon.

In general, when the length of a VCSEL (or LED) is close to the average size of the particulates, Mie-Debye scattering is stronger than Rayleigh scattering and light-scattering sensors have a high sensitivity to particulates with diameters approximately equal to the VCSEL wavelength, and low sensitivity to particulates much smaller than the VCSEL wavelength. In the embodiment disclosed in FIG. 6, for example, since carbon and metal particulates have larger size difference, the two VCSELs 602 and 604 (or LED) can be utilized. One VCSEL is IR VCSEL 602, and the other is UV VCSEL 604 (e.g., 130 nm, 100 nm or even smaller). Note that although an IR VCSEL 602 and a UV VCSEL 604 are depicted in FIG. 6, one or more LED's can be implemented in place of or in addition to IR VCSEL 602 and UV VCSEL 604. Thus, although the use of a VCSEL is preferred, other types of light-emitting devices may be utilized in place such a VCSEL(s), while still following within the scope and spirit of the invention claimed herein.

Note that one non-limiting example of a VCSEL, which can be adapted for use in implementing VCSEL 602 and/or 604 and hence light-emitting device 408, is disclosed in U.S. Pat. No. 6,875,993, entitled "Systems and Methods for Optically Detecting and Identifying Objects in an Environment," which issued to Tatum et al. on Apr. 5, 2005. U.S. Pat. No. 6,875,993, which is assigned to Honeywell International Inc., is incorporated herein by reference.

U.S. Pat. No. 6,875,993 generally discloses a vertical cavity surface emitting laser (VCSEL) structure with a plurality of emission apertures. Such Emission apertures can be fabricated by using either proton isolation or dielectric oxide techniques to provide both carrier and optical confinement. Upon powering elements, emission apertures emit light signals perpendicular to the VCSEL structure, making them especially amenable to the fabrication of both one and two-dimensional (or more) arrays.

Another non-limiting example of a VCSEL for use in implementing VCSEL 602 and/or 604 and hence light-emitting device 408, is disclosed in U.S. Pat. No. 6,817,528, entitled "Reflective Apparatus and Method for Optically Sensing Relative Torque Employing Moire Fringes," which issued to Bo Su Chen on Nov. 16, 2005. U.S. Pat. No. 6,817,528, which is incorporated herein by reference, is assigned to Honeywell International Inc.

U.S. Pat. No. 6,817,528 discusses the use of a vertical cavity surface emitting laser (VCSEL) units as the source of identical beams of uncollimated laser light. Such a VCSEL is one type of light source that can be utilized in accordance with the embodiments disclosed herein. Other types of light sources can also be utilized in accordance with one or more embodiments. For example, the light source 602, 604 and/or 408 may be configured as other types of lasers, including an edge emitting laser, a light-emitting diode, or an incandescent lamp. The uncollimated laser light can be emitted in the form of an uncollimated laser beam.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An oil quality sensor apparatus, comprising:
   a housing;
   an oil flow path that said oil flows through said housing; and
   a plurality of photo-detectors and a plurality of light-emitting devices located within said housing proximate to said oil flow path, wherein at least one photo-detector device among said plurality of photo-detector devices is sensitive to large particulates associated with said oil and at least one other photo-detector device among said plurality of photo-detector devices is sensitive to small particulates associated with said oil to thereby provide an indication of size differences among particulates associated with said oil, and
   wherein at least one light-emitting device among said plurality of light-emitting devices has a wavelength approximately equivalent to a size of large particulates associated with said oil and at least one other light-emitting device among said plurality of light-emitting devices has a wavelength approximately equivalent to a size of small particulates associated with said oil to thereby provide an indication of differences among particulates associated with said oil, and
   wherein said housing is further configured to comprise a plurality of light absorption components, wherein each light absorption component among said plurality of light absorption components respectively faces each light-emitting device among said plurality of light-emitting devices.

2. The apparatus of claim 1 wherein said plurality of light-emitting devices comprises a plurality of VCSELs.

3. The apparatus of claim 1 wherein said at least one light-emitting device among said plurality of light-emitting devices comprises an IR VCSEL and said at least one other light-emitting device among said plurality of light-emitting devices comprises a UV VCSEL.

4. The apparatus of claim 3 wherein said IR VCSEL possesses a wavelength that is approximately equivalent to a size of a metal particulate associated with said oil and said UV VCSEL possesses a wave length that is approximately equivalent to a size of a carbon particulate associated with said oil.

5. The apparatus of claim 1 wherein said plurality of light-emitting devices comprises a plurality of edge emitting lasers, wherein each edge emitting laser among said plurality of edge emitting lasers possesses a different wave-length.

6. The apparatus of claim 1 wherein said plurality of light-emitting devices comprises a plurality of LEDs, wherein each LED among said plurality of LEDs possesses a different wave-length.

7. The apparatus of claim 1 wherein said plurality of photo-detector devices comprises a plurality of photo-diodes wherein each photo-diode among said plurality of photo-diodes possesses a different wave-length.

8. An oil quality sensor apparatus, comprising:
   a housing;
   an oil flow path that said oil flows through said housing; and
   a plurality of photo-detectors and a plurality of VCSELs located within said housing proximate to said oil flow path, wherein at least one photo-detector among said plurality of photo-detectors is sensitive to large particulates associated with said oil and at least one other photo-detector among said plurality of photo-detectors is sensitive to small particulates associated with said oil to thereby provide an indication of differences among particulates associated with said oil, and
   wherein at least one VCSEL device among said plurality of VCSEL devices possesses a wavelength that is approximately equivalent to a size of large particulates associated with said oil and at least one other VCSEL device among said plurality of VCSEL devices possesses a wavelength that is approximately equivalent to a size of small particulates associated with said oil to thereby provide an indication of differences among particulates associated with said oil, and
   wherein said housing is further configured to comprise a plurality of light absorption components, wherein each light absorption component among said plurality of light absorption components respectively faces each VCSEL among said plurality of VCSELs.

9. The apparatus of claim 8 wherein each VCSEL among said plurality of VCSELS possesses a different wave-length.

10. The apparatus of claim 8 wherein said at least one VCSEL among said plurality of VCSELS comprises an IR VCSEL and said at least one other VCSEL among said plurality of VCSELS comprises a UV VCSEL.

11. The apparatus of claim 10 wherein said IR VCSEL possesses a wave length that is approximately equivalent to a median size of said large particulates.

12. The apparatus of claim 11 wherein said large particulates comprise metal.

13. The apparatus of claim 10 wherein said UV VCSEL possesses a wave length close that is approximately equivalent to a median size of said small particulates.

14. The apparatus of claim 13 wherein said small particulates comprise carbon.

15. The apparatus of claim 10 wherein said plurality of photo-detector devices comprises a plurality of photo-diodes wherein each photo-diode among said plurality of photo-diodes possesses a different wave-length.

16. An oil quality sensing method, comprising:
providing a housing;
configuring said housing to include an oil flow path wherein said oil flows through said housing; and
locating a plurality of photo-detectors and a plurality of light-emitting devices within said housing proximate to said oil flow path, wherein at least one photo-detector device among said plurality of photo-detector devices is sensitive to large particulates associated with said oil and at least one other photo-detector device among said plurality of photo-detector devices is sensitive to small particulates associated with said oil to thereby provide an indication of size differences among particulates associated with said oil, and
wherein at least one light-emitting device among said plurality of light-emitting devices possesses a wavelength approximately close to a size of large particulates associated with said oil and at least one other light-emitting device among said plurality of light-emitting devices possesses a wavelength that is approximately close to a size of small particulates associated with said oil to thereby provide an indication of differences among particulates associated with said oil, and
further configuring housing to comprise a plurality of light absorption components, wherein each light absorption component among said plurality of light absorption components respectively faces each light-emitting device among said plurality of light-emitting devices.

17. The method of claim 16 further comprising providing said configuring said plurality of light-emitting devices to comprise a plurality of VCSELs, wherein each VCSEL among said plurality of VCSELs comprises a different wave-length.

18. The method of claim 16 further comprising further comprising configuring said plurality of light-emitting devices to comprise a plurality of edge emitting lasers, wherein each edge emitting laser among said plurality of edge emitting lasers possesses a different wave-length.

19. The method of claim 16 further comprising configuring said plurality of light-emitting devices to comprise a plurality of LEDs, wherein each LED among said plurality of LEDs possesses a different wave-length.

20. The method of claim 16 further comprising configuring said plurality of photo-detector devices to comprise a plurality of photo-diodes wherein each photo-diode among said plurality of photo-diodes possesses a different wave-length.

* * * * *